United States Patent [19]
Bodanszky

[11] 3,957,760

[45] May 18, 1976

[54] AMINO ACID DERIVATIVES

[75] Inventor: Miklos Bodanszky, Shaker Heights, Ohio

[73] Assignee: E. R. Squibb & Sons, Inc., Princeton, N.J.

[22] Filed: Apr. 9, 1973

[21] Appl. No.: 349,503

Related U.S. Application Data

[63] Continuation of Ser. No. 98,939, Dec. 16, 1970, abandoned, Continuation-in-part of Ser. No. 798,790, Feb. 12, 1969, abandoned, which is a continuation-in-part of Ser. No. 451,609, April 28, 1965, abandoned.

[52] U.S. Cl. .......................... 260/239.3 T; 260/333; 260/293.59; 260/239.3 B; 260/534 S; 260/287 R

[51] Int. Cl.$^2$ ........................................ C07D 498/08

[58] Field of Search .............................. 260/239.3 T

*Primary Examiner*—Natalie Trousof
*Assistant Examiner*—Robert T. Bond
*Attorney, Agent, or Firm*—Lawrence S. Levinson; Merle J. Smith; Burton Rodney

[57] ABSTRACT

New lactone intermediates useful in the synthesis of peptides are prepared by reacting an α-amino acid with an active carbonyl compound which forms a Schiff's base. The latter is treated with a condensing agent so that cyclization occurs and a lactone is formed from which a peptide may be produced by reaction with an amino acid ester and removal of the protecting groups.

5 Claims, No Drawings

AMINO ACID DERIVATIVES

This application is a continuation of copending application Ser. No. 98,939, filed Dec. 16, 1970, now abandoned, which application is a continuation-in-part of copending application Ser. No. 798,790, filed Feb. 12, 1969, now abandond, which in turn is a continuation-in-part of application Ser. No. 451,609, filed Apr. 28, 1965, now abandoned.

This invention relates to new intermediates useful in the synthesis of peptides. More particularly, the invention relates to amino acid derivatives, especially derivatives of α-amino acids, which are simultaneously protected and activated for reaction with other amino acids in the synthesis of peptides.

In the usual synthesis of peptides, two amino acids are joined "head to tail", i.e., the carbonyl group of the acid moiety of one amino acid is joined to the amino group of the second amino acid. It is conventional in such a synthesis to protect the reactive amino group of one amino acid with a readily removable protective group such as a benzyloxycarbonyl, t-butyloxycarbonyl, phthalyl, tosyl group, etc., so that the amino group does not enter into the reaction. Then the carbonyl group of the same amino acid is activated with another group, e.g., with an azide or with an ester group such as the p-nitrophenyl ester, so that the carbonyl group will react with or acylate the amino group of the second amino acid in the presence of the protecting group.

This procedure, it is evident, requires two distinct reactions with two separate compounds in preparation of the one amino acid for the ultimate reaction with the second amino acid. It further requires the combination of two proper groups which will give the desired protection and activation of the particular amino acid involved.

BRIEF SUMMARY OF THE INVENTION

It has now been found that α-amino acids can be both protected and activated by reacting the amino acid with a single compound and then forming a lactone. This method and the novel lactones formed thereby form the essence of this invention. These lactones readily react with α-amino acid esters to form condensation products from which the protecting-activating moiety is readily removed to leave the desired peptide.

Briefly, the method comprises reacting an α-amino acid with an active carbonyl compound which forms a Schiff's base and then the Schiff's base is treated with a condensing agent to induce cyclization and yield a lactone of the formula

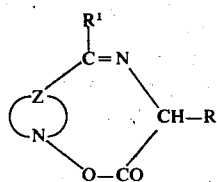

wherein R is the residue of an α-amino acid, $R^1$ is hydrogen or lower alkyl, and Z taken with N is a heterocyclic ring or a condensed ring system wherein a heterocyclic ring is condensed with a benzene ring.

DETAILED DESCRIPTION OF THE INVENTION

Any α-amino acid may be treated according to this invention. This includes the naturally occurring α-amino acids [see for example, Hackh's Chemical Dictionary, 3rd ed. (1944), pages 44–45] as well as synthetic α-amino acids. Some examples are monoaminocarboxylic aliphatic acids, e.g., glycine, α-aminoheptylic acid, α-aminocaprylic acid, α-aminononylic acid, α-aminodecylic acid, α-aminoundecylic acid, alanine, serine, cysteine, threonine, methionine, valine, leucine, isoleucine; aromatic monoaminomonocarboxylic acids, e.g., phenylalanine, tyrosine, dihydroxyphenylalanine, 3,5-dibromotyrosine, 3-iodotyrosine, 3,5-diiodotyrosine, 3,5,3'-triiodotyronine, and thyroxine; monoaminodicarboxylic acids and their amides, e.g., aspartic acid, glutamic acid, asparagine and glutamine; diaminomonocarboxylic acids, e.g., lysine, hydroxylysine, ornithine and arginine; heterocyclic amino acids, e.g., histidine, tryptophane, proline, hydroxyproline, thiolhistidine; diaminodicarboxylic acids, e.g., cystine, lanthionine and djenkolic; as well as α-amino acids of the same type found in special sources, e.g., phenylglycine, butyrine, citrulline, homocystine, hypoglycin A, S-methylcysteine sulfoxide, alliin and canavanine.

Other amino acids are aminomalonic acid, α-aminoadipic acid, α-aminopimelic acid, α-aminosuberic acid, α-aminosebacic acid, β-hydroxyaspartic acid, cystine-β,β-dicarboxylic acid, β-hydroxyglutamic acid, β-methylaspartic acid, β-methyl-β-hydroxyaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, α-aminotricarballyic acid, β-aminoalanine, γ-aminobutyrine, homoarginine, homocitrulline, α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, α,α'-diaminosebacic acid, α,α'-diaminodecanedicarboxylic acid, α,α'-diaminododecanedicarboxylic acid, γ-methylproline, pipecolic acid, baikiain, 5-hydroxypipecolic acid, azetidine-2-carboxylic acid, β-phenylserine, canaline, γ-oxalysine, γ-hydroxyornithine, and 2-hexosaminic acids. A comprehensive discussion of amino acids, including those mentioned above, is to be found in *Chemistry of the Amino Acids*, Greenstein et al., Vol. III, Wiley, 1961. Other amino acids in addition to those listed above are to be found in this volume but for sake of brevity are not specifically mentioned herein but are included by reference. It is to be understood that the present invention is applicable to any amino acid.

The amino acid of the formula

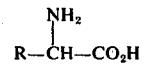

wherein R is the residue of the amino acid is reacted with a carbonyl compound to produce a Schiff's base. These carbonyl compounds are aldehydes or ketones having the structural formula

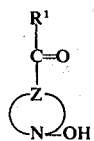

wherein $R^1$ is hydrogen or a straight or branched chain lower alkyl radical of from 1 to 4 carbon atoms, and Z taken with the nitrogen atom to which it is joined (N)

is a heterocyclic ring wherein the ring is formed from 5 or 6 atoms or a condensed ring system wherein a heterocyclic ring as previously defined in condensed with a benzene ring.

Examples of suitable aliphatic carbonyl compounds are the following:

α-formyl-N-hydroxysuccinimide
N-hydroxy-β-formylpyrrole
N-hydroxy-β-formyl-2,5-dimethylpyrrole
4-acetyl-N-hydroxypiperidine
N-hydroxy-3-formylphthalimide The amino acid is reacted with the aldehyde or ketone in an inert solvent, preferably an inert organic solvent such as dimethylformamide, dioxane, pyridine or the like under conventional conditions for forming a Schiff's base. Then, after the Schiff's base has formed, without isolating the base unless desired, a condensing agent is added to the reaction mixture to form the lactone. An alcohol may also be used as the reaction medium in which the Schiff's base is formed, but in this case the solvent must be removed before adding the condensing agent.

Any condensing agent which promotes the formation of acyl esters may be used. These include, for example, dicycloalkylcarbodiimides, e.g., dicyclohexylcarbodiimide; dialkylcarbodiimides, e.g., dipropylcarbodiimide; diarylcarbodiimides, e.g., diphenylcarbodiimide; alkoxyacetylenes, e.g., ethoxyacetylene, diphenylketene, etc. Dicyclohexylcarbodiimide and ethoxyacetylene are preferred. About one mol or more of condensing agent per mol of Schiff's base may be used. A mol ratio of about 1:1 may be used when the condensing agent is a carbodiimide. An excess of the condensing agent is preferable when other condensing agents are used.

Sufficient time must elapse for the Schiff's base to form before the condensing agent is introduced. The time period may vary within rather broad limits depending upon the particular reactants, but a period of about one hour to about twenty-four hours is generally adequate. Stirring and/or heating will of course accelerate the reaction. Temperatures in the range of about 15° to 60°C. may be used.

The cyclization reaction which occurs upon addition of the condensing agent must be effected in an anhydrous medium and the solvent must be one which has no reactive hydroxy or carboxy group. Media such as those named above, except alcohols, may be used for the cyclization as well. Room temperature up to about 60°C. may be used, with a temperature in the lower end of the range preferred for carbodiimides and a temperature at the higher end of the range for alkoxyacetylenes.

According to one modification, the amino acid and aldehyde are dissolved in the solvent and stirred for about one hour to twenty-four hours. Then, without isolating the Schiff's base, or after merely concentrating the solution, the condensing agent is added.

The active lactones of this invention will then react with another amino acid, preferably a simple ester thereof, such as a lower alkyl ester whereupon the ring opens and the amino acid is acylated. Treatment with aqueous acid, e.g., with hydrochloric acid, dilute sulfuric acid or the like, removes the protecting groups and the desired peptide is obtained.

It will be appreciated that the process of this invention is not limited to the formation of dipeptides from monomeric amino acids but applies as well to the formation of polypeptides from reactants having more than one amino acid moiety, e.g., the formation of tripeptides, tetrapeptides, pentapeptides, hexapeptides, octapeptides, decapeptides, etc. When the amino acid used has another reactive functional group elsewhere in the molecule, this may have to be independently protected in the conventional manner.

The following examples illustrate the invention without, however, limiting the same thereto. All temperatures given are in degrees Centigrade.

EXAMPLE 1

2-Hydroxy-5-nitrobenzylidene-L-leucine and its Lactone

L-Leucine (2.62 g.) and 5-nitrosalicylaldehyde (5.0 g.) are added to a mixture of absolute ethanol (750 ml.) and methanol (50 ml.). The mixture is stirred at room temperature for several hours. When all the leucine is dissolved, the solvents are removed in vacuo. The residue extracted with ether, the ether extracts concentrated and diluted with hexane. A crystalline solid separates. It is filtered and washed with hexane. The crude Schiff base (dec. at ca. 175°–189° completely melting at ca. 200°) is used in the cyclization step without additional purification. The benzylidene derivative (1.40 g.) is dissolved in tetrahydrofuran (40 ml.) and dicyclohexylcarbodiimide (1.03 g.) is added to the solution. After about two hours at room temperature, the completion of the reaction is checked with the IR spectrum of a sample (disappearance of the strong band at 4.8 μ, corresponding to the CN bond of the diimide, and appearance of the carbonyl band of the active ester at 5.65 μ). The by-product, mainly N,N'-dicyclohexylurea, is removed by filtration and washed with tetrahydrofuran (20 ml.). The filtrate and washings are concentrated in vacuo to dryness, the residue is dissolved in ether, and the solution is diluted with hexane. The active ester is obtained in good yield in the form of crystals with strong double refraction. The product has a poorly defined melting point.

The lactone obtained above and glycine ethyl ester are reacted in chloroform. Dilute hydrochloric acid is added to the reaction mixture and L-leucyl glycine ethyl ester is obtained as the product.

EXAMPLE 2

2-Hydroxy-5-chlorobenzylidene-L-alanine lactone

5-Chlorosalicylaldehyde (0.157 g.) and L-alanine (0.91 g.) are added to dimethylformamide (10 ml.). After 24 hours at room temperature dicyclohexylcarbodiimide (0.206 g.) is added to the solution. The formation of a CO band at 5.65μ reaches its maximum in about 2 hours. The precipitated dicyclohexylurea is removed by centrifugation and the active lactone which has the structural formula

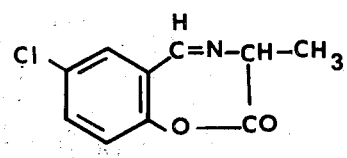

is precipitated by the addition of ether (50 ml.) to the decanted supernatant solution (IR 5.65μ).

EXAMPLE 3

L-Phenylalanine (0.165 g.) and 3-formyl-N-hydroxyphthalimide (0.19 g.) are suspended in methanol and the mixture is stirred until complete solution occurs. The methanol is removed in vacuo, tetrahydrofuran (3 ml.) and ethoxyacetylene (3 ml.) are added to the residue and the resulting solution is heated to boiling under reflux condenser for one hour. The solvent and the excess ethoxyacetylene are removed in vacuo, tetrahydrofuran (3 ml.) and ethoxyacetylene (3 ml.) are added to the residue and the resulting solution is heated to boiling under a reflux condenser for one hour. The solvent and the excess ethoxyacetylene are removed in vacuo and the residue is triturated with ether to yield the active lactone (IR 5.6$\mu$) having the formula

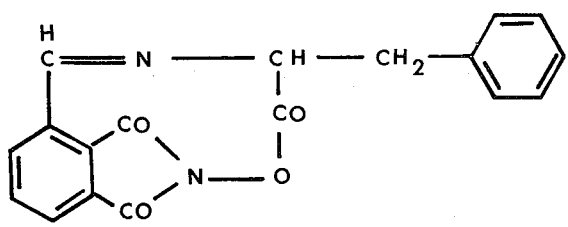

EXAMPLE 4

L-Serine (0.105 g.) is reacted with $\alpha$-formyl-N-hydroxysuccinimide (0.15 g.) as described in Example 3. The schiff base is obtained by removing the solvent and then reacting with ethoxyacetylene to obtain the active lactone (IR 5.6$\mu$) having the formula

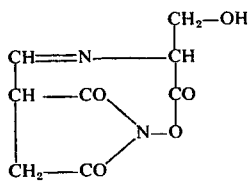

EXAMPLE 5

L-Glutamine (1.5 g.) and 4-acetyl-N-hydroxypiperidine (1.5 g.) are stirred in ethanol (100 ml.) for 24 hours. The solvent is removed in vacuo and the residue is treated with dicyclohexylcarbodiimide (2.1 g.) in tetrahydrofuran (20 ml.). After 3 hours at room temperature, the precipitated N,N'-dicyclohexylurea is removed by centrifugation and the supernatant solution, which contains the active lactone having the structural formula

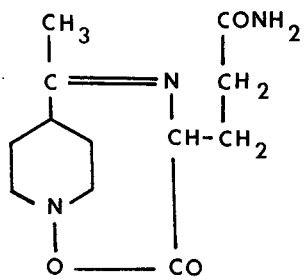

is used for the synthesis of glutaminyl derivatives.

EXAMPLE 6

To a solution of the Schiff base from 2,4-pentadione and methionine having the formula

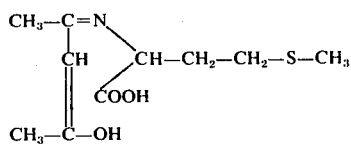

(23.2 g.) in dimethylformamide (200 ml.), dicyclohexylcarbodiimide (21 g.) is added. After two hours at room temperature, the precipitated N,N'-dicyclohexylurea is filtered off and the filtrate which contains the active lactone (IR 5.56$\mu$) having the formula

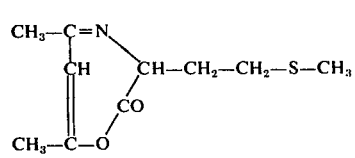

is used in peptide synthesis.

EXAMPLES 7–26

Following the procedure of Example 3, but protecting reactive side chains where necessary and substituting for L-phenylalanine the amino acid indicated in column I, and for 3-formyl-N-hydroxyphthalimide the carbonyl compound indicated in column II, there is obtained the compound (or mixture of compounds) of formula I wherein the substituents R, $R^1$, $R^2$, $R^3$ and m are as indicated in column III:

| | I | II | | III | | | |
|---|---|---|---|---|---|---|---|
| Example | Amino Acid | Carbonyl Compound | R | $R^1$ | $R^2$ | $R^3$ | m |
| 7 | L-glycine | malondialdehyde | —H | —H | —H | —H | 0 |
| 8 | L-alanine | 3-ketobutyral | { —CH$_3$ | —H | —H | —CH$_3$ | 0 |
| | | | —CH$_3$ | —CH$_3$ | —H | —H | 0 |
| 9 | L-serine | | { —CH$_2$OH | —H | —H | —CH$_3$ | 0 |
| | | | —CH$_2$OH | —CH$_3$ | —H | —H | 0 |
| 10 | L-glycine | succindialdehyde | —H | —H | —H | —H | 1 |
| 11 | L-glycine | 4-ketopentanal | { —H | —H | —H | —CH$_3$ | 1 |
| | | | —H | —CH$_3$ | —H | —H | 1 |
| 12 | L-cysteine | glutardialdehyde | —CH$_2$SH | —H | —H | —H | 2 |
| 13 | L-threonine | 4-ketohexanal | { —CH(OH)—CH$_3$ | —H | —H | —CH$_2$CH$_3$ | 1 |
| | | | —CH(OH)—CH$_3$ | —CH$_2$CH$_3$ | —H | —H | 1 |
| 14 | L-glycine | adipaldehyde | —H | —H | —H | —H | 3 |

-continued

| Example | I<br>Amino Acid | II<br>Carbonyl Compound | R | III<br>R¹ | R² | R³ | m |
|---|---|---|---|---|---|---|---|
| 15 | L-valine | 2,4-hexanedione | $-CH\begin{matrix}CH_3\\CH_3\end{matrix}$ | $-CH_2CH_3$ | $-H$ | $-CH_3$ | 0 |
|  |  |  | $-CH\begin{matrix}CH_3\\CH_3\end{matrix}$ | $-CH_3$ | $-H$ | $-CH_2CH_3$ | 0 |
| 16 | L-isoleucine | 2,5-hexanedione | $-\underset{\underset{CH_3}{\vert}}{CH}-CH_2-CH_3$ | $-CH_3$ | $-H$ | $-CH_3$ | 1 |
| 17 | L-aspartic | 2-methyl-3-ketopentanal | $-CH_2-CO_2H$ | $-H$ | $-CH_3$ | $-CH_2CH_3$ | 0 |
|  |  |  | $-CH_2-CO_2H$ | $-CH_2CH_3$ | $-CH_3$ | $-H$ | 0 |
| 18 | L-glycine | 2-methyl-4-ketopentanal | $-H$ | $-H$ | $-H$ | $-CH_3$ | 1 |
|  |  |  | $-H$ | $-CH_3$ | $-H$ | $-CH_3$ | 0 |
| 19 | L-glycine | 3-methylpentanedial | $-H$ | $-H$ | $-H$ | $-H$ | 2 |
| 20 | L-alanine | octanedial | $-CH_3$ | $-H$ | $-H$ | $-H$ | 5 |
| 21 | L-alanine | pentanedial | $-CH_3$ | $-H$ | $-H$ | $-H$ | 7 |
| 22 | L-glycine | 2-methyl-4-ketohexa-3-ene-6-al | $-H$ | $-H$ | $-H$ | $=CH-CH\begin{matrix}CH_3\\CH_3\end{matrix}$ | 0 |

EXAMPLES 23–33

Following the procedure of Example 1, but protecting the reactive side chains where necessary and substituting for L-leucine the amino acid indicated in column I and for 5-nitrosalicylaldehyde the carbonyl compound indicated in column II, there is obtained the compound of the following formula

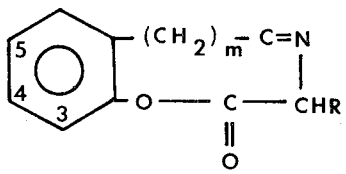

wherein the substituent R is the residue of the amino acid indicated in column I and wherein the substituent in the 3-, 4- or 5-position is the same as that of the starting salicylaldehyde, and m has the value indicated in column III.

| Example | I | II | III |
|---|---|---|---|
| 23 | L-lysine | salicylaldehyde | 0 |
| 24 | L-hydroxylysine | 3-chlorosalicylaldehyde | 0 |
| 25 | L-cysteine | 5-chlorosalicylaldehyde | 0 |
| 26 | L-tyrosine | 3-bromosalicylaldehyde | 0 |
| 27 | L-tryptophane | 4-bromosalicylaldehyde | 0 |
| 28 | L-proline | 5-bromosalicylaldehyde | 0 |
| 29 | L-histidine | 5-isodosalicylaldehyde | 0 |
| 30 | L-hydroxyproline | 3-nitrosalicylaldehyde | 0 |
| 31 | L-glycine | 5-nitrosalicylaldehyde | 0 |
| 32 | L-alanine | o-hydroxyphenylacetaldehyde | 1 |
| 33 | L-alanine | o-hydroxyphenylpropionaldehyde | 2 |

What is claimed is:
1. A compound of the formula

wherein R is the R group of an α-amino acid, $$R-\underset{\underset{NH_2}{\vert}}{CH}-COOH$$

selected from the group consisting of naturally occurring α-amino acids and derivatives thereof wherein there are substituents selected from the group consisting of lower alkyl, hydroxy, halogen and amino, R¹ is hydrogen or straight or branched chain alkyl of from 1 to 4 carbon atoms, and

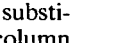

is

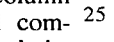

2. A method for preparing a compound of claim 1 comprising reacting an α-amino acid of the formula $$R-\underset{\underset{NH_2}{\vert}}{CH}-CO_2H$$

wherein R is the residue of the amino acid as defined in claim 1 with a carbonyl compound of the formula

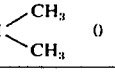

wherein

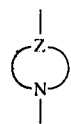

is as defined in claim 1, to form a Schiff's base the reaction taking place in an inert organic solvent at a temperature of from about 15° to about 60°C and then adding a carbodiimide or alkoxyacetylene condensing agent under anhydrous conditions at from about room temperature to about 60°C to the Schiff's base to form a lactone.

3. A compound according to claim 1 wherein the amino acid is phenylalanine.

4. A method according to claim 2 wherein the amino acid is phenylalanine and the carbonyl compound is N-hydroxy-3-formylphthalimide.

5. A compound according to claim 1 wherein R' is H and R is

* * * * *

UNITED STATES PATENT AND TRADEMARK OFFICE
CERTIFICATE OF CORRECTION

PATENT NO. : 3,957,760
DATED : May 18, 1976
INVENTOR(S) : Miklos Bodanszky

It is certified that error appears in the above-identified patent and that said Letters Patent are hereby corrected as shown below:

Column 4, line 24, "189°" should read --180°--.
Column 5, line 33, "schiff" should read --Schiff--.

Signed and Sealed this

Seventh Day of September 1976

[SEAL]

Attest:

RUTH C. MASON
Attesting Officer

C. MARSHALL DANN
Commissioner of Patents and Trademarks